(12) United States Patent
Teng et al.

(10) Patent No.: US 11,535,762 B2
(45) Date of Patent: Dec. 27, 2022

(54) FAST DRYING AQUEOUS AMINE FREE COATING COMPOSITION(S)

(71) Applicant: Ennis-Flint, Thomasville, NC (US)

(72) Inventors: George Ganghua Teng, Greensboro, NC (US); Robert W. Greer, Lexington, NC (US); Kevin Newell, Greensboro, NC (US)

(73) Assignee: Ennis Flint, Thomasville, NC (US)

( * ) Notice: Subject to any disclaimer, the term of this patent is extended or adjusted under 35 U.S.C. 154(b) by 0 days.

(21) Appl. No.: 13/841,888

(22) Filed: Mar. 15, 2013

(65) Prior Publication Data

US 2014/0079888 A1    Mar. 20, 2014

Related U.S. Application Data

(60) Provisional application No. 61/702,458, filed on Sep. 18, 2012.

(51) Int. Cl.

| | | |
|---|---|---|
| *C09D 7/45* | (2018.01) | |
| *C09D 133/12* | (2006.01) | |
| *C09D 153/02* | (2006.01) | |
| *C09D 5/02* | (2006.01) | |
| *C08F 220/14* | (2006.01) | |
| *C08G 59/14* | (2006.01) | |
| *C09D 7/63* | (2018.01) | |
| *C08G 73/02* | (2006.01) | |
| *C07D 251/30* | (2006.01) | |
| *C08K 5/3492* | (2006.01) | |
| *E01F 9/518* | (2016.01) | |
| *C07C 209/68* | (2006.01) | |
| *C07C 215/08* | (2006.01) | |
| *C07C 227/02* | (2006.01) | |
| *C07C 229/16* | (2006.01) | |
| *C07D 403/14* | (2006.01) | |
| *C09D 5/14* | (2006.01) | |
| *C09D 5/00* | (2006.01) | |
| *C08K 5/103* | (2006.01) | |
| *C08K 5/17* | (2006.01) | |

(52) U.S. Cl.
CPC .............. *C09D 7/45* (2018.01); *C07C 209/68* (2013.01); *C07C 215/08* (2013.01); *C07C 227/02* (2013.01); *C07C 229/16* (2013.01); *C07D 251/30* (2013.01); *C07D 403/14* (2013.01); *C08F 220/14* (2013.01); *C08G 59/1477* (2013.01); *C08G 73/0206* (2013.01); *C08K 5/3492* (2013.01); *C08K 5/34924* (2013.01); *C08K 5/34926* (2013.01); *C09D 5/024* (2013.01); *C09D 5/14* (2013.01); *C09D 7/63* (2018.01); *C09D 133/12* (2013.01); *C09D 153/02* (2013.01); *E01F 9/518* (2016.02); *C08K 5/103* (2013.01); *C08K 5/17* (2013.01); *C08K 5/175* (2013.01); *C09D 5/00* (2013.01)

(58) Field of Classification Search
CPC ...... C09D 133/12; C09D 7/1233; C09D 7/45; C09D 153/02; C09D 5/024; C09D 7/63; C09D 5/14; C09D 5/00; C08F 220/14; C08G 59/1477; C08G 73/0206; C07D 251/30; C07D 403/14; C08K 5/34924; C08K 5/3492; C08K 5/34926; C08K 5/103; C08K 5/17; C08K 5/175; E01F 9/518; C07C 209/68; C07C 215/08; C07C 227/02; C07C 229/16
USPC ...................................................... 427/393.6
See application file for complete search history.

(56) References Cited

U.S. PATENT DOCUMENTS

| | | |
|---|---|---|
| 4,150,005 A | 4/1979 | Gehman et al. |
| 4,265,745 A | 5/1981 | Kawaguchi et al. |
| 5,084,505 A | 1/1992 | Biale |
| 5,731,377 A | 5/1998 | Friel |
| 5,922,398 A | 7/1999 | Hermes et al. |
| 6,031,038 A | 2/2000 | Baumstark et al. |
| 6,846,867 B2 | 1/2005 | Gebhard et al. |
| 6,875,834 B2 | 4/2005 | Gray et al. |
| 6,930,143 B2 | 8/2005 | Harris et al. |
| 7,001,949 B2 | 2/2006 | Fasano et al. |
| 7,094,826 B2 | 8/2006 | Martin et al. |
| 7,235,595 B2 | 6/2007 | Hermes et al. |
| 9,499,714 B2 | 11/2016 | Li et al. |
| 2001/0009952 A1 | 7/2001 | Tan et al. |
| 2004/0260005 A1* | 12/2004 | Gould .................. C08F 285/00 524/501 |
| 2007/0148357 A1 | 6/2007 | Joecken et al. |
| 2008/0058473 A1* | 3/2008 | Freidzon et al. ............. 525/191 |

(Continued)

FOREIGN PATENT DOCUMENTS

CN    102295824    12/2011

OTHER PUBLICATIONS

U.S. Appl. No. 14/856,917 , "Final Office Action", dated Feb. 7, 2019, 4 pages.

(Continued)

*Primary Examiner* — Robert S Walters, Jr.

(74) *Attorney, Agent, or Firm* — Kilpatrick Townsend & Stockton LLP

(57) ABSTRACT

Coating compositions and methods providing a high build, fast drying, fast hardening non-amine containing aqueous latex binders are provided, wherein the coating composition is applied to a substrate at a wet film thickness to about 15 mils that ensure drying times of less than 10 minutes. The binder requires the use of at least one specific coalescent solvent with both anionic and non-anionic surfactants.

15 Claims, No Drawings

(56) References Cited

U.S. PATENT DOCUMENTS

2012/0065323 A1\* 3/2012 Overton .................... C08F 2/24
 524/559
2014/0235752 A1\* 8/2014 Gharapetian et al. ........ 523/201

OTHER PUBLICATIONS

U.S. Appl. No. 14/856,917 , "Final Office Action", dated Jan. 10, 2018, 6 pages.
U.S. Appl. No. 14/856,917 , "Non Final Office Action", dated May 29, 2018, 5 pages.
U.S. Appl. No. 15/284,700 , "Non Final Office Action", dated Oct. 9, 2018, 7 pages.
U.S. Appl. No. 15/284,700 , "Notice of Allowance", dated Mar. 28, 2019, 10 pages.
U.S. Appl. No. 15/284,700 , "Restriction Requirement", dated May 8, 2018, 9 pages.

\* cited by examiner

FAST DRYING AQUEOUS AMINE FREE COATING COMPOSITION(S)

PRIORITY

This application claims the benefit of and priority to U.S. Provisional Patent Application No. 61/702,458 filed on Sep. 18, 2012, the entirety of which is incorporated herein.

BACKGROUND OF THE INVENTION

Aqueous latex binders are fluid systems which contain polymer particles distributed in stable disperse form as the disperse phase in the aqueous dispersing medium. Aqueous polymer emulsions have the ability to form polymer films on evaporation of the aqueous dispersing medium, and it is for this reason that these emulsions are widely used as binders for surface coatings. The type of dispersed polymer and the temperature at which film formation takes place determine whether an aqueous polymer emulsion forms a cohesive film or a brittle, easily cracked layer after the evaporation of water. The lowest temperature at which a crack-free film is just formed is referred to as the minimum film formation temperature (MFFT) of the relevant composition.

It is generally known that aqueous emulsions of polymers that contain only polymerized monomers with homopolymers that have low glass transition temperatures, Tg, are known as soft monomers that are capable of forming polymer films at proper and sufficiently low temperatures. However, a disadvantage of the resulting films is that they are too soft and too tacky for many applications, and such films readily become soiled and loose permanence quickly.

It is also generally known that aqueous emulsions of polymers that contain essentially only polymerized hard monomers (monomers with homopolymers have a high glass transition temperature, Tg) generally require a high temperature for film formation.

In the area of traffic paint, for example, it is desirable to use aqueous compositions that can be applied in a single coat thick application (i.e., high build), yet can dry and harden soon after application under ambient conditions and have high water resistance in the finished coatings. Problems that have been experienced with various waterborne traffic marking paint formulations include slow dry times and relatively poor durability, particularly when such formulations have been applied under humid conditions.

SUMMARY OF THE INVENTION

The present disclosure provides to a high build, fast drying and fast hardening aqueous coating composition suitable for use as a pavement or road marking traffic paint for concrete or asphalt roads, walkways, or parking lots, or a coating for masonry, wood and other building material substrates. The high build aqueous coating composition of this invention utilizes a latex binder formed by emulsion polymerization of hard monomers and soft monomers with an acid-functional monomer in an aqueous medium. The aqueous latex binder in accordance with this invention is used in combination with a coalescing solvent having appropriate characteristics to provide coatings having very rapid dry times without the use of amine groups in either the binder or the paint compositions.

Typically, the dry film thickness of coatings of this invention is about 15 mils which represents a significant improvement over any previously known compositions in that that the drying time of these high build paints is reduced to below 10 minutes as measured by ASTM test method D711-2010 without the use of amines in the binder formulation and durability is not sacrificed. In the binder formulations of present invention there is no need for adjusting the pH using ammonia or ammonium hydroxide because there are no polyamine interactions with the anionic surfactants (that are used to stabilize the emulsion). Polyfunctional amines require full deprotonization to ensure no reaction with the anionically stabilized (binder) polymer emulsion and anionic ingredients in the final paint formulation. In the case of the present invention, because there are no functional amine groups added to the binder (latex emulstion), the requirements for deprotonization described above are unnecessary, however shelf life as well as fast dry times have not been compromised of the final paint (coating) formulations.

The aqueous coating compositions of this invention also have excellent adhesion to high traffic surfaces such as concrete, masonry, stone and brick. The compositions of this disclosure also relates to a method for providing a high build, fast drying and fast hardening aqueous coating.

More specifically, this invention relates to a high build, fast drying and fast hardening aqueous coating composition comprising: (a) a latex binder comprising: about 35 to about 65% by weight, based on said latex binder weight, of at least one hard monomer; about 25 to about 55% by weight, based on said latex binder weight, of at least one soft monomer; and about 0.5 to about 15% by weight, based on said latex binder weight, of at least one acid functional monomer; about 0.5 to about 4% by active weight, based on the latex binder weight, of at least one anionic surfactant and one non-anionic surfactant the combination of which is about 1 to 4 active weight percent based on the total monomer weight; wherein said latex binder has a glass transition temperature less than 45° C. and a resulting average particle size diameter of at least 210 nanometers to about 290 nanometers; and (b) at least one coalescing solvent that is 2,2,4-trimethyl-1,3-pentanediol monoisobutyrate. Based on the formulations, the high and low carboxyl functional latex have theoretical acid number around 17 and 5, respectively, and the carboxyl functional monomer weight percentage based on total "active" weight is between 2.5 to 3.1% and 0.6 to 0.7, respectively. The concentration for the surfactants in the examples provided varies from 14% (SDS) to 70% (CA407), and surfactant with same chemical structure can have different concentrations. For example, SDS generally has been commonly used in several concentrations, such as 22, 28, and 50%. To better define surfactant efficiency, "active" weight percentage is often used to define surfactant concentration.

This invention also relates to a method of producing a high build coating on a surface comprising: (I) applying to said surface a layer of an aqueous coating composition comprising: (a) a latex binder comprising: about 35 to about 65% by weight, based on said latex binder weight, of at least one hard monomer; about 25 to about 55% by weight, based on said latex binder weight, of at least one soft monomer; and about 0.5 to about 15% by weight, based on said latex binder weight, of at least one acid functional monomer; about 0.5 to about 4% by active weight, based on said latex binder weight, of at least one anionic and one non-anionic surfactant of 1 to 4 active weight percent based on the total monomer weight; wherein said latex binder has a glass transition temperature less than 45° C. and an average particle size diameter of between about 210 nanometers and about 290 nanometers; and (b) at least one coalescing solvent that is 2,2,4-trimethyl-1,3-pentanediol monoisobutyrate.

DETAILED DESCRIPTION OF THE INVENTION

The high build fast hardening coating compositions of this invention as applied to a substrate at a wet film thickness of about 15 mils, have very rapid dry times, lower film formation temperatures, higher moisture resistance, higher crack resistance, and high solids content and hardness in the applied dried paints. One of the aspects to obtaining the excellent characteristics lies in the combination of the aqueous latex binder of this invention with the proper coalescing solvent(s) as well as the proper use of both anionic and non-anionic surfactants with appropriate characteristics and in proper concentrations. Heretofore, it has not been possible to employ 15 mil films with drying times of less 10 minutes at 20 C or above without the use of amines in the binder formulation.

In accordance with this invention, the coating composition comprises a latex binder comprising at least one hard monomer, at least one soft monomer, and an acid functional monomer. The latex binder comprises about 35 to about 65 weight percent hard monomer, about 25 to about 55 weight percent soft monomer, about 0.5 to about 12 weight percent acid functional monomer, and about 1.0 to about 10.0 active weight percent of the total combination of the non-anionic and anionic surfactant, all based on the total weight percent of the latex binder.

With respect to the hard monomer, the term "hard monomer" generally means a monomer whose homopolymer has a glass transition temperature (Tg) of greater than 30° C. and includes, but is not limited to non-functional methacrylic monomers such as methyl methacrylate, ethyl methacrylate, isopropyl methacrylate, isobutyl methacrylate, isobornyl methacrylate, and mixtures thereof and alkenyl aromatic monomers such as styrene, p-methyl styrene, methyl styrene, o-methyl styrene, o,p-dimethyl styrene, o,p-diethyl styrene, p-chlorostyrene, o-methyl-p-isopropyl styrene, o,p-dichlorostyrene, isopropyl styrene, t-butyl styrene, and mixtures thereof.

The preferred hard monomer is methyl methacrylate.

The term "soft monomer" generally means a monomer whose homopolymer has a Tg of less than about −20° C., and includes nonfunctional acrylic monomers such as methyl acrylate, ethyl acrylate, butyl acrylate, isobutyl acrylate, ethyl hexyl acrylate, isodecyl methacrylate, lauryl methacrylate, tridecylmethacrylate, and mixtures thereof. The preferred soft monomer is butyl acrylate.

The polymerization of these monomers can optionally include other ethylenically unsaturated copolymerizable comonomers. Also, optionally, the polymerization may be in the presence of other crosslinking monomers.

Surfactants useful in the present invention are both anionic surfactants and non-ionic surfactants. Anionic surfactants include, but are not limited to, alkylphenolethoxylate sulfates and sulfonates, alkysulfates and sulfonates, such as ammonium lauryl ether sulfate, alkali alkylether sulfates such as sodium lauryl ether sulfate, octyl phenol ethoxylates, sodium lauryl sulfate, phosphate esters, and mixtures thereof. Non-anionic surfactants include for example; octyl phenol ethoxylate, alkyl ethylene oxide/propylene oxide copolymers. Generally, the emulsion comprises weight percent anionic surfactant and 0.5 to 1.5 active weight percent of the non- about 0.5 to 2.5 active anionic surfactant based on the weight of the monomer. Preferably, the range of the total non-anionic and anionic surfactant is between 4 and 17 weight percent. As used herein, the "weight percent surfactant" is defined as the total dry weight of the surfactant(s) used in making the polymer emulsion divided by the total weight of the monomers used in making the polymer.

The latex binder of the invention has a Tg of less than 45° C. and an average particle size of between 210 nanometers to 290 nanometers. The solids content of the latex binder is generally at least about 40 weight percent, preferably within the range of about 45 to about 60 weight percent, and more preferably within the range of 45 to about 55 weight percent.

At least one coalescing solvent is added to the latex binder. Aqueous latex paints cure by a process known as coalescence where first the water, and then the trace, or coalescing, solvent, evaporate and draw together and soften the binder particles and fuse them together into irreversibly bound networked structures, so that the paint will not redissolve in the solvent/water that originally carried it. The solvent can be selected by one skilled in the art based on desired minimum film formation temperature, dry time and desired water resistance, or other desired characteristics of the final paint composition. Some examples of coalescing solvents include alkyl alcohol ethoxylates such as propyl glycol n-propyl ether (PnP), propylene glycol methyl ether (PM), dipropylene glycol methyl ether (DPM), ethylene glycol monopropyl ether (EP), dipropylene glycol monobutyl ether (DPnB), propylene glycol (PG), diethylene glycol monobutyl ether (butyl carbitol), 2,2,4-trimethyl-1,3-pentanediol monoisobutyrate (commercially available as Eastastripe from Eastman Chemical, Eastman, Tenn.), and methanol. Of the various coalescing solvents that can be used, 2,2,4-trimethyl-1,3-pentanediol monoisobutyrate, which possesses a high film integrity at low levels, enhances a lower temperature of formation and scrub resistance and is not classified as a VOC, and has been found to provide low toxicity and the required solvent of choice for these formulations The emulsion polymers described are prepared in the form of aqueous dispersions in a conventional manner by emulsion polymerization in an aqueous medium in the presence of a free radical oxygen-containing initiator in which the monomers are mixed with the surfactants prior to being fed into the reaction vessel. The latex binders may also be prepared by other conventional methods such as simultaneous feed of the monomer mixture and surfactant mixture into the reactor and by the core/shell method.

It is preferred to add an initiator to the polymer emulsion composition. Exemplary initiators include, but are not limited to, t-butyl hydroperoxide, sodium persulfate, ammonium persulfate, hydrogen peroxide, and mixtures thereof. Particular suitability for preparing finely divided dispersions are alkali metal salts or ammonium salts such as sodium carbonate or ammonium persulfate, which in general is used in amounts of about 0.25 to 1% by weight based on the total weight of binder.

A final coating paint formulation typically also comprises a dispersing aid, thickening aids, a biocide, pigments, extenders and fillers, and a defoamer as shown in Tables 5 and 6.

A lower acid level is desirable for decreased water sensitivity of the final coating. While not intending to be bound to any theory, a lower acid number for the coating composition may help control the latex particle size, stability, water solubility and Tg. For traffic paints, in particular, a lower acid number can be advantageous on the heat age stability, freeze/thaw stability, dry time and scrub resistance. The high build aqueous coating compositions can be applied to surfaces of high traffic areas at high film thicknesses, normally 2 to 15 mils wet film thickness, and allowed to dry at ambient conditions. Typically, the dry film thickness of coatings of this invention is about 15 mils which represents a significant improvement over any previously known compositions in that that the drying time of these high build paints is reduced to below 10 minutes without the use of amines in the binder formulation and durability is not sacrificed. In the binder formulations of present invention there is no need for adjusting the pH using ammonia or ammonium hydroxide because there are no polyamine interactions with the anionic surfactants (that are used to stabilize the emulsion). Polyfunctional amines require full deprotonization to ensure no reaction with the anionically stabilized (binder) polymer emulsion and anionic ingredients in the final paint formulation. In the case of the present invention, because there are no functional amine groups added to the binder (latex emulstion), the requirements for deprotonization described above are unnecessary, however shelf life as well as fast dry times have not been compromised of the final paint (coating) formulations.

The coating formulations of this invention have a fast dry time, fast hardening and early water resistance and produce crack-free coating films. The resulting coating has improved dirt resistance and release, and is highly suitable for use as a fast dry coating for floors and other high traffic hard surfaces such as concrete, masonry, stone, brick. In addition, the surfaces can be smooth, rough, and/or porous, and upon drying, the coating composition forms a smooth film. The novel latex paint and binder formulations described herein have coalescing solvent loading between 1.7% and 2.5%, and with Tg's between 23 and 36 degrees Centigrade for the dry latex.

EXAMPLES

The following examples demonstrate the preparation of exemplary latex binders within the scope of the invention, as well as paint compositions formulated using these latex binders. Unless otherwise stated, "percent" means percent-by-weight.

As used herein, the following abbreviations and terms have the following meanings IGEPAC CA407, octylphenenol ethoxylate, received from Rhodia.

Stepan-Mild SL3-BA, disodium laureth sulfosuccinate, received from Stepan.

Aerosol A102, disodium ethoxylated alcohol half ester of sulfosucnic acid, received from Cytec.

SDS, sodium dodecyl sulfate, purchased from Aldrich.

Tamol 901, Anionic polyelectrolyte/polyacid pigment dispersant, available from XXXX Surfynol CT-136, acetylenic diol anionic surfactant blend, available from Air Products Corp., Allentown, Pa.

Drewplus L-493, contain methylated silica and silica colloidal amorphous (Ashland Chemical)

Ti-Pure R-900, Titanium Dioxide (TiO2), available from DuPont

Omyacarb-5, Calcium carbonate, available from Omya North America

Natrosol 250HR (2% aqueous), a Water soluble cellulose, 2-hydroxyethylether, available from Ashland, Inc.

Bayferrox 3950, an inorganic pigment, available from Bayferrox.

Example A

Preparation of 35° C. Tg Latex Binder Formulation

The monomer mixture of butyl acrylate (BA), methyl methacrylate (MMA), and methacrylic acid (MAA), as shown below in Table 1 was slowly added into a flask containing a stirring water solution of NaHCO$_3$, Aerosol A-102, CA407, and deionized water to obtain a monomer pre-emulsion. An initiator solution was prepared by dissolving ammonium persulfate (3.52 g) in deionized water (160 g). The monomer pre-emulsion (128 g) and initiator solution (64.8 g) were charged into the reaction flask with NaHCO$_3$ (0.5 g) and Aerosol A-102 (1.4 g). The contents were stirred for 0.5 h at 80° C. bath temperature to form seed latex particles. The remaining pre-emulsion mixture and initiator were concurrently added into the seed latex at a constant rate over a period of 3 h. The polymerization was maintained at 80° C. under nitrogen. After the addition of all ingredients, the contents were heated at 80° C. for an additional 2 h in order to digest all the residual monomers. The latex was then filtered through a 300 mesh screen to remove any residual coagulum.

The glass transition temperature of the latex binder is 35° C. Tg. Based on the formulations, the high and low carboxyl functional latex have theoretical acid number around 17 and 5, respectively, and the carboxyl functional monomer percentage in all the monomers around 4.5% and 1.3%, respectively.

TABLE 1

| Components | Function | Weight, g |
|---|---|---|
| BA | Monomer | 210 |
| MMA | Monomer | 250 |
| MAA | Carboxyl monomer | 23 |
| NaHCO$_3$ | Buffer | 0.5 |
| Aerosol A-102, 31% active | Surfactant | 17 |
| IGEPAL CA-407, 70% active | Surfactant | 4.3 |
| Water | Solvent | 257 |

Example B

Preparation of 23° C. Tg Latex Binder Formulation

The monomer mixture of BA, MMA, and MAA, as shown below in Table 2 was slowly added into a flask containing a stirring water solution of NaHCO$_3$, Stepan SL3-BA, CA407, and deionized water to obtain a monomer pre-emulsion. An initiator solution was prepared by dissolving ammonium persulfate (3.52 g) in deionized water (160 g). The monomer pre-emulsion (128 g) and initiator solution (64.8 g) were charged into the reaction flask with NaHCO$_3$ (0.5 g) and Stepan SL3-BA (1.4 g). The contents were stirred for 0.5 h at 80° C. bath temperature to form seed latex particles. The remaining pre-emulsion mixture and initiator were concurrently added into the seed latex at a constant rate over a period of 3 h. The polymerization was maintained at 80° C. under nitrogen. After the addition of all ingredients, the contents were heated at 80° C. for an additional 2 h in order to digest all the residual monomers. The latex was then filtered through a 300-mesh screen to remove any residual coagulum.

TABLE 2

| Components | Function | Weight, g |
| --- | --- | --- |
| BA | Monomer | 210 |
| MMA | Monomer | 250 |
| MAA | Carboxyl monomer | 23 |
| NaHCO$_3$ | Buffer | 0.5 |
| Stepan SL3-BA, 30% active | Surfactant | 17 |
| IGEPAL CA-407, 70% | Surfactant | 4.3 |
| Water | Solvent | 257 |

Example C

Preparation of 29° C. Tg Latex Binder

The monomer mixture of BA, MMA, and MAA, as shown below in Table 4 was slowly added into a flask containing a stirring water solution of NaHCO$_3$, SDS, CA407, and deionized water to obtain a monomer pre-emulsion. An initiator solution was prepared by dissolving ammonium persulfate (3.52 g) in deionized water (160 g). The monomer pre-emulsion (128 g) and initiator solution (64.8 g) were charged into the reaction flask with NaHCO$_3$ (0.8 g) and SDS (2.8 g). The contents were stirred for 0.5 h at 80° C. bath temperature to form seed latex particles. The remaining pre-emulsion mixture and initiator were concurrently added into the seed latex at a constant rate over a period of 3 h, and then 50 g water was added. The polymerization was maintained at 80° C. under nitrogen. After the addition of all ingredients, the contents were heated at 80° C. for an additional 2 h in order to digest all the residual monomers. The latex was then filtered through a 300-mesh screen to remove any residual coagulum.

TABLE 3

| Components | Function | Weight, g |
| --- | --- | --- |
| BA | Monomer | 315.9 |
| MMA | Monomer | 379 |
| MAA | Carboxyl monomer | 9 |
| NaHCO$_3$ | Buffer | 0.8 |
| SDS, 14% active | Surfactant | 102.4 |
| CA-407, 70% active | Surfactant | 12.8 |
| Deionized water | Solvent | 400 |

Table 4 below summarizes the characteristics of the binder composition in use with the final waterborne coating formulation (paint). This also lists the coalescent solvent to be used for the coating. The dryer times are significantly lower than those of conventional binders and coatings that contain polyfunctional amines. The concentration for the surfactants in the examples provided (A-C in Tables 1, 2, and 3) varies from 14% (SDS) to 70% (CA407), and surfactant with same chemical structure can have different concentrations. For example, SDS generally has been commonly used in several concentrations, such as 22, 28, and 50%. To better define surfactant efficiency, "active" weight percentage is often used to define surfactant concentration.

TABLE 4

| | Example A | Example B | Example C |
| --- | --- | --- | --- |
| Tg of Emulsion | 35.3° C. | 23.3° C. | 29° C. |
| Total Weight | 927.22 g | 927.22 g | 1387.0 g |
| Hard Monomer Wt % | 27.0% | 27.0% | 27.3% |
| Soft Monomer Wt % | 22.6% | 22.6% | 22.8% |
| Carboxyl Monomer Wt % | 2.48% | 2.48% | 0.65% |
| Anionic Surfactant (active Wt % of monomer weight) | 1.1% | 1.1% | 2.0 |
| Nonionic Surfactant (active Wt % of monomer weight) | 0.6% | 0.6% | 1.3% |
| Total active Surfactant Wt % | 1.7% | 1.7% | 3.3% |
| Particle Size (nm) | 283 | 215 | 253 |
| MFFT | 16° C. | 8° C. | 15° C. |
| Coalescent solvent | Eastastripe | Eastastripe | Eastastripe |
| Dry Time | 6.5 min | 7.5 min | 9 min |

Formulation of Coatings

The latex binders of Examples A through C have been formulated into each of the waterborne fast dry coating compositions according to the paint formulas which are presented in Tables 5 and 6. The solvents for the use of these fast drying amine free compositions are subject to change as drying times required may also change over time. Tables 5 and 6 provide final finished white and yellow coating (paint) formulations using the amine free binder compositions of the present invention and themselves represent novel and unique coatings used primarily for road surfaces. The binder in the coatings (paint) formulation is only latex which is generated from monomers, initiator, buffer, surfactants, and water using the synthesis process as mentioned above, and eventually contains polymer, buffer, surfactant, and water. Anything other than latex adding during the paint formulation, like coalescing solvent and surfactant, are not directly part of the binder formulation. The high and low carboxyl functional latex formulations possess theoretical acid numbers around 17 and 5, respectively, and the carboxyl functional monomer weight percentage based on total weight is between 2.3 to 3.0% and 0.60 to 0.7%, respectively.

TABLE 5

Fast-Dry White Traffic Paint Formulation

| Components | Function | Weight, pounds |
| --- | --- | --- |
| Order of Addition | | |
| Latex, 45-60% solids | Binder | 460.1 |
| Tamol 901 | Dispersant | 7.2 |
| Surfynol CT-136 | Surfactant | 2.8 |
| Drew L-493 | Defoamer | 2.0 |
| Ti-Pure R-900 (TiO2) | White pigment | 100.0 |
| Omyacarb-5 (Calcium carbonate) | Filler | 760.6 |
| Mix the above at a sufficient speed for about 15 minutes, then add: | | |
| Methanol | Solvent | 30.0 |
| Eastastripe | Coalescing solvent | 23.0 |
| Drew L-493 | Defoamer | 3.5 |
| Natrosol 250HR (2% aqueous) | Thickener | 7.0 |
| Water | Solvent | 11.6 |

TABLE 6

Fast-Dry Yellow Traffic Paint Formulation

| Components | Function | Weight, pounds |
|---|---|---|
| Order of Addition | | |
| Latex, 45-60% solids | Binder | 470.8 |
| Tamol 901 | Dispersant | 7.2 |
| Surfynol CT-136 | Surfactant | 2.8 |
| Drew L-493 | Defoamer | 2.0 |
| Ti-Pure R-900 (TiO2) | White pigment | 20.0 |
| Omyacarb-5 (Calcium carbonate) | Filler | 750.0 |
| Hansa Yellow 11-2400 | Yellow pigment | 32.0 |
| Bayferrox 3950 | Yellow pigment | 3.0 |
| Mix the above at a sufficient speed for about 15 minutes, then add: | | |
| Methanol | solvent | 30.0 |
| Eastastripe | Coalescing solvent | 23.0 |
| Drew L-493 | Defoamer | 3.5 |
| Natrosol 250HR (2% aqueous) | Thickener | 6.0 |
| Water | Solvent | 5.0 |

Although the invention has been described in considerable detail with reference to certain preferred versions thereof; other versions are possible. For example, the coating compositions can include one or more ingredients that enhance other film properties such as gloss, durability. Therefore, the spirit and scope of the claims should not necessarily be limited to the description of the preferred embodiments contained herein.

What is claimed is:

1. An amine free aqueous coating composition comprising:
    an amine free latex binder; and
    only one coalescing solvent,
    wherein the amine free latex binder comprises at least one anionic surfactant, a non-ionic surfactant, and a polymer prepared from at least one hard monomer, at least one soft monomer, and at least one acid functional monomer, the amounts of the monomers and the anionic surfactant being:
        (i) 35 to 65% by weight of the at least one hard monomer, based on a total weight of said latex binder;
        (ii) 25 to 55% by weight of the at least one soft monomer, based on the total weight of said latex binder weight;
        (iii) 0.5 to 15% by weight of the at least one acid functional monomer, based on the total weight of said latex binder weight; and
        (iv) 0.1% to 4% by weight of the at least one anionic surfactant, based on the total weight of said latex binder weight;
    wherein said latex binder has a glass transition temperature less than 45 degrees Centigrade, and wherein said latex binder is amine free, ammonia free, and ammonium hydroxide free, and has an average particle size diameter consisting of between 210 nanometers and 290 nanometers, and
    wherein said coating composition exhibits a drying time of less than 10 minutes as measured by ASTM test method D711-2010.

2. The composition of claim 1, wherein the glass transition temperature of the latex binder is between 23 degrees Centigrade and 36 degrees Centigrade.

3. The composition of claim 1, wherein said composition is operable to be dried at ambient temperature when the composition is applied to a surface at or above 15 mils film thickness.

4. The composition of claim 1, wherein the coalescing solvent is selected from the group consisting of: propyl glycol n-propyl ether, propylene glycol methyl ether, dipropyl glycol methyl ether, ethylene glycol monopropyl ether, dipropylene glycol monobutyl ether, propylene glycol, diethylene glycol monobutyl ether, trimethyl pentanediol monoisobutyrate, and methanol.

5. The coating composition of claim 1, wherein said hard monomer comprises a methacrylic monomer.

6. The coating composition of claim 1, wherein said soft monomer comprises butyl acrylate.

7. The composition of claim 1, wherein the at least one acid functional monomer is present in an amount between 2.5 and 3.1 weight percent, based on the total weight of said latex binder weight, and the latex binder has an acid number of 17.

8. The composition of claim 1, wherein said latex binder has an average particle size diameter consisting of between 250 nanometers and 290 nanometers.

9. An amine free aqueous coating composition comprising: only one coalescing solvent; and
    an amine free latex binder comprising a surfactant and a polymer prepared from at least one hard monomer, at least one soft monomer, and at least one acid functional monomer, the amounts of the monomers and the surfactant being:
        (i) 35 to 65% by weight of the at least one hard monomer, based on a total weight of said latex binder;
        (ii) 25 to 55% by weight of the at least one soft monomer, based on the total weight of said latex binder;
        (iii) 0.5 to 15% by weight of the at least one acid functional monomer, based on the total weight of said latex binder;
        (iv) 1 to 10% by active weight of the surfactant, based on the total weight of said latex binder, wherein the surfactant comprises at least one non-ionic surfactant and at least one anionic surfactant;
    wherein the coating composition is substantially free of amine, ammonia, and ammonium hydroxide, and wherein the coating composition has a drying time of less than 10 minutes as measured by ASTM test method D711-2010.

10. The composition of claim 9, wherein the latex binder has a glass transition temperature less than 45 degrees Centigrade.

11. The composition of claim 9, wherein the latex binder has a glass transition temperature of between 23 degrees Centigrade and 36 degrees Centigrade.

12. The composition of claim 9, wherein the coating composition comprises particles having an average particle size diameter of between 210 nanometers and 290 nanometers.

13. The composition of claim 9, wherein at least one acid functional monomer is present in an amount between 2.5 and 3.1 weight percent, based on the total weight of latex binder.

14. The composition of claim 9, wherein said coating composition is operable to be dried at ambient temperature when the composition is applied to a surface at or above 15 mils film thickness.

15. The composition of claim 9, wherein the latex binder has an acid number of 17.

\* \* \* \* \*